(12) United States Patent
Palushi et al.

(10) Patent No.: US 11,607,341 B2
(45) Date of Patent: Mar. 21, 2023

(54) FLEXIBLE PATULOUS EUSTACHIAN TUBE IMPLANT WITH INTEGRATED VENTING

(71) Applicant: Acclarent, Inc., Irvine, CA (US)

(72) Inventors: Jetmir Palushi, Irvine, CA (US); Fatemeh Akbarian, Rancho Palos Verdes, CA (US); John H. Thinnes, Jr., Mission Viejo, CA (US)

(73) Assignee: Acclarent, Inc., Irvine, CA (US)

( * ) Notice: Subject to any disclaimer, the term of this patent is extended or adjusted under 35 U.S.C. 154(b) by 256 days.

(21) Appl. No.: 17/020,880

(22) Filed: Sep. 15, 2020

(65) Prior Publication Data
US 2021/0085525 A1 Mar. 25, 2021

Related U.S. Application Data

(60) Provisional application No. 62/902,489, filed on Sep. 19, 2019.

(51) Int. Cl.
*A61F 2/18* (2006.01)
*A61F 11/20* (2022.01)

(52) U.S. Cl.
CPC ..... *A61F 11/202* (2022.01); *A61F 2210/0004* (2013.01); *A61F 2220/0016* (2013.01); *A61F 2250/0067* (2013.01)

(58) Field of Classification Search
CPC ......... A61F 11/20–202; A61F 2/04–2002/048; A61B 17/12036–12104
See application file for complete search history.

(56) References Cited

U.S. PATENT DOCUMENTS

| | | | |
|---|---|---|---|
| 4,650,488 A | 3/1987 | Bays et al. | |
| 5,819,745 A | 10/1998 | Mobley et al. | |
| 6,589,286 B1 | 7/2003 | Litner | |
| 8,197,552 B2 | 6/2012 | Mandpe | |
| 10,206,821 B2 | 2/2019 | Campbell et al. | |
| 10,350,396 B2 | 7/2019 | Chan et al. | |
| 2009/0099573 A1* | 4/2009 | Gonzales | A61F 11/202 606/108 |
| 2010/0174366 A1* | 7/2010 | Avior | A61F 11/202 623/10 |
| 2010/0274188 A1 | 10/2010 | Chang et al. | |
| 2012/0095527 A1 | 4/2012 | Vardi et al. | |
| 2013/0274715 A1 | 10/2013 | Chan et al. | |
| 2017/0340485 A1 | 11/2017 | Verhoeven et al. | |
| 2019/0060125 A1 | 2/2019 | Ngo-Chu et al. | |
| 2020/0069472 A1* | 3/2020 | Palushi | A61L 29/16 |
| 2020/0069473 A1 | 3/2020 | Palushi et al. | |

* cited by examiner

*Primary Examiner* — Rebecca S Preston
(74) *Attorney, Agent, or Firm* — Frost Brown Todd LLP (57) ABSTRACT

An implant that may maintain position with a Eustachian tube of a patient, the implant includes an engagement body, an anchoring assembly, and a pressure balance assembly. The engagement body includes an exterior surface dimensioned to bear radially outward against the Eustachian tube. The anchoring assembly may lock the implant in the Eustachian tube. The pressure balance assembly includes a vented pathway that may transition between an occluded state and a vented state. The vented pathway may provide fluid communication between the proximal end and the distal end of the implant in the ventilated state while inhibiting fluid communication between the proximal end and the distal end of the implant in the occluded state.

17 Claims, 9 Drawing Sheets

FLEXIBLE PATULOUS EUSTACHIAN TUBE IMPLANT WITH INTEGRATED VENTING

PRIORITY

This application claims priority to U.S. Provisional Pat. App. No. 62/902,489, entitled "Flexible Patulous Eustachian Tube Implant with Integrated Venting," filed Sep. 19, 2019, the disclosure of which is incorporated by reference herein.

BACKGROUND

Figure 1:
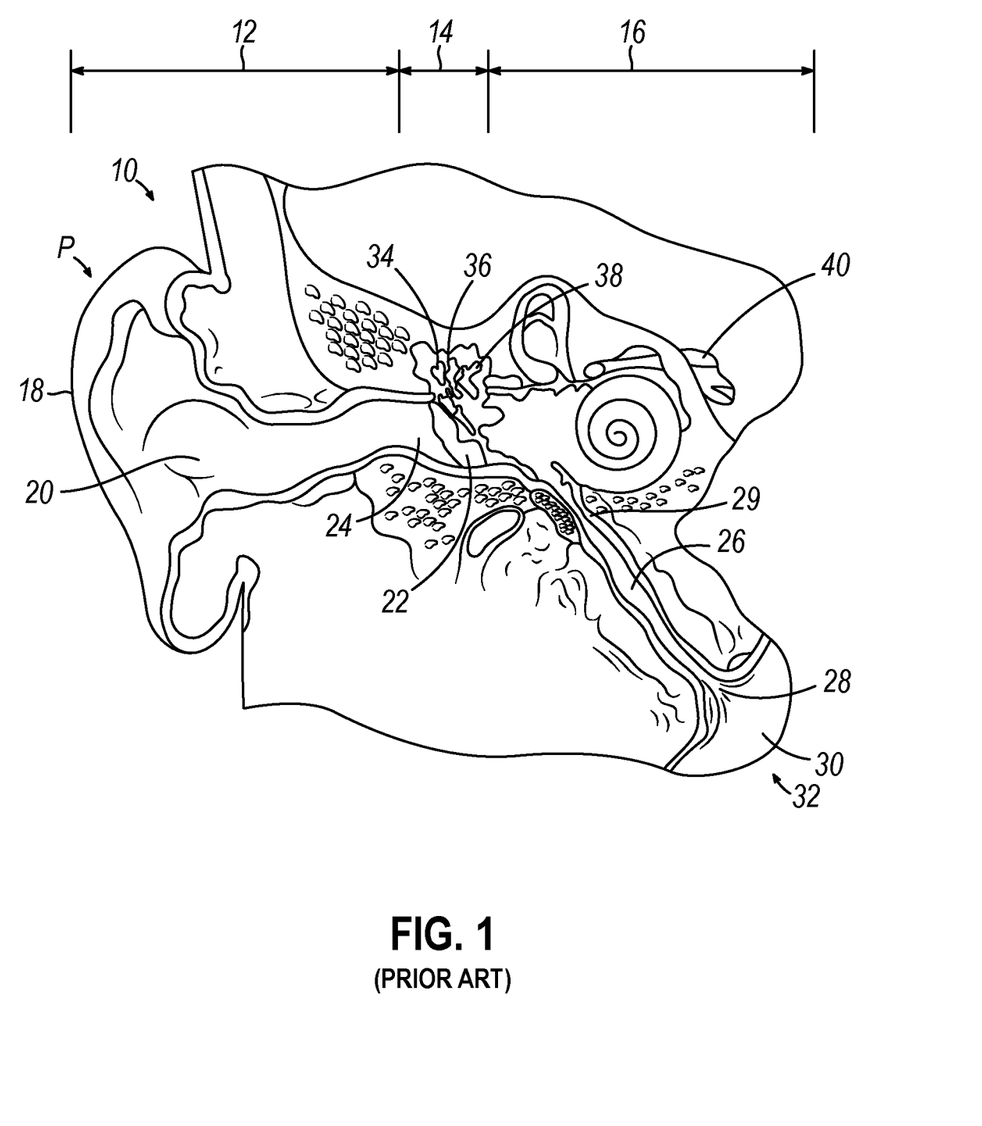
FIG. 1 depicts a cross-sectional view of a human ear showing the inner, middle and outer ear portions and the Eustachian tube connecting the middle ear with the nasopharynx region of the throat.

Referring to FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. A narrowed region known as the isthmus (29) of the ET (26) provides a transition between the remainder of the ET (26) and the middle ear (14). The isthmus (29) is the narrowest part of the ET (26) at the junction of the bony and cartilaginous parts of the ET (26) (i.e., where the bony canal meets the cartilaginous tube). The isthmus (29) thus has a reduced inner diameter compared to the remaining portion of the ET (26) that extends between the isthmus (29) and the pharyngeal ostium (28); and provides a density that is substantially greater than the density of the tissue of the remaining portion of the ET (26) that extends between the isthmus (29) and the pharyngeal ostium (28).

The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This may occur frequently in children in connection with an upper respiratory infection and account for hearing impairment associated with this condition.

When the ET (26) is blocked, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Finally, the fluid can become infected, which can lead to pain, illness, and temporary hearing loss. If the inner ear (14) is affected, the patient may feel a spinning or turning sensation (vertigo).

Methods for treating the middle ear (14) and restriction or blockage of the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pat. No. 10,350,396, entitled "Vent Cap for a Eustachian Tube Dilation System," issued Jul. 16, 2019, the disclosure of which is incorporated by reference herein.

In some cases, rather than being restricted or blocked, the ET (26) may fail to close properly, or such that the ET (26) takes an inordinately prolonged amount of time to close after being opened, such that the ET (26) substantially remains in a patulous state. This may adversely affect a patient by causing variations in the upper airway pressure around the ET (26) and the middle ear (14). In some patients, a patulous ET (26) may create a feeling of dry sinus, an increased breathing rate with physical activity, higher than usual perceived volumes of sound, and/or other undesirable consequences. It may therefore be desirable to provide a form of treatment for a patulous ET (26). It may further be desirable for such a treatment to still provide some degree of ventilation and drainage for the ET (26), without completely closing the ET (26).

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Implants and Methods of Treating the Eustachian Tube

As noted above, some patients may have an ET (26) that remains patulous for a prolonged period, which may be undesirable for various reasons. In some instances, if a patulous ET (26) is maintained in a radially outwardly stressed state (as comparted to ET (26) in the patulous state) for a prolonged period of time (e.g. nine to twelve months), the prolonged stress may trigger a process were cells within ET (26) regenerate such that ET (26) transitions from the undesirable patulous state toward a more desirable, normal functioning state. For instance, imposing a radially outward stress on the ET (26) may generate scar tissue in the ET (26). It may therefore be desirable to insert an implant or other device into a patulous ET (26) of a patient, where the inserted implant or other device is capable of bearing radially outwardly against the sidewall of a patulous ET (26) for a prolonged period of time. It may also be desirable to have an implant or other device that is sufficiently flexible to conform to the anatomy shape of a patulous ET (26), or various other anatomical passageways, after or during deployment. Further, it may be desirable to have an implant or other device that is made of bioabsorbable materials configured to bio-absorb after a desired prolonged period of time, such that there is no need for removal of the implant or other device after deployment.

As also mentioned above, a normal function ET (26) functions as a pressure equalizing valve for the middle ear (14), which is normally filled with air. In particular, the ET (26) opens for a fraction of a second periodically to allow air into the middle ear (14) to replace air that has been absorbed by the middle ear lining (mucous membrane) or to equalize pressure changes occurring on altitude changes. Therefore, in some instances, it may be desirable to insert an implant or other device into a patulous ET (26) of a patient, where the implant assists the patulous ET (26) in functioning as a pressure equalizing valve between the middle ear (14) and the pharyngeal ostium (28). It may also be desirable to insert an implant or other device into a patulous ET (26) of a patient, where the implant provides a ventilation pathway along a patulous ET (26) between the middle ear (14) and the pharyngeal ostium (28).

The following description provides various examples of devices and implants that may be deployed within the ET (26) to bear outwardly against the inner diameter of the ET (26) for a prolonged period of time while providing pressure relief between the middle ear (14) and the pharyngeal ostium (28). Such devices may treat a dysfunctional ET (26), repair a patulous ET (26), occlude a leaking ET (26) (e.g., a cerebrospinal fluid leak, etc.), treat a chronic ear disease, or provide other results. Other suitable ways in which the below-described implants and/or devices may be used will be apparent to those of ordinary skill in the art in view of the teachings herein.

A. Exemplary Implant with Collapsible Ventilation Features

Figure 2:
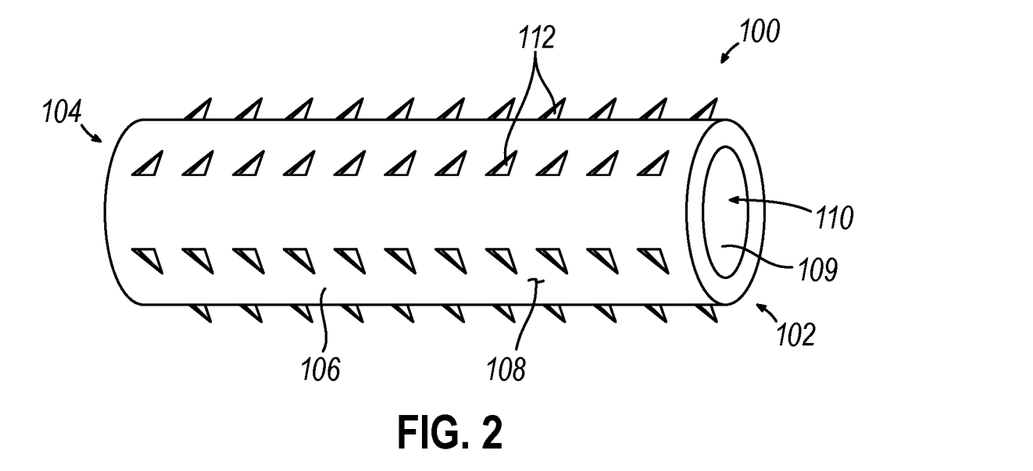
FIG. 2 depicts a perspective view of an exemplary implant.
Figure 3:
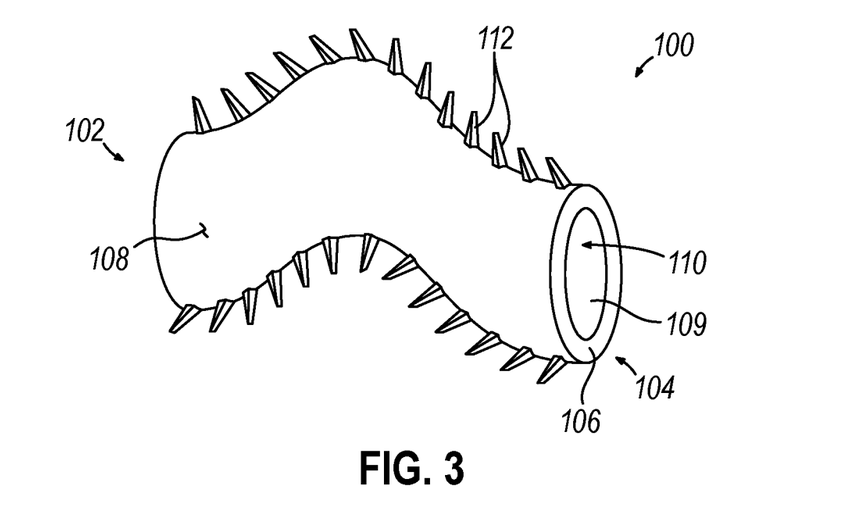
FIG. 3 depicts another perspective view of the implant of FIG. 2.

FIGS. 2-3 shows an exemplary implant (100) that may be deployed within ET (26). As will be described in greater detail below, implant (100) is configured to impose a radially outward stress on an interior wall (27) of a patulous ET (26) while selectively providing ventilation along ET (26) between the middle ear (14) and the pharyngeal ostium (28) when implant (100) is suitably deployed. Implant (100) includes a conformable body (106) and a plurality of barbs (112) extending from an exterior surface (108) of conformable body (106).

Barbs (112) are connected to and extend outwardly away from exterior surface (108) of conformable body (106). Barbs (112) also extend proximally at angles that are oblique to the longitudinal axis of implant (100). In the current example, barbs (112) are disposed about conformable body (106) in multiple linear arrays, which are disposed circumferentially about exterior surface (108). However, barbs (112) may be disposed about exterior surface (108) in any suitable arrangement as would be apparent to one skilled in the art in view of the teachings herein. Barbs (112) are configured to anchor interior wall (207) of ET (26) when deployed such that implant (100) is secured within ET (26).

Figure 4A:
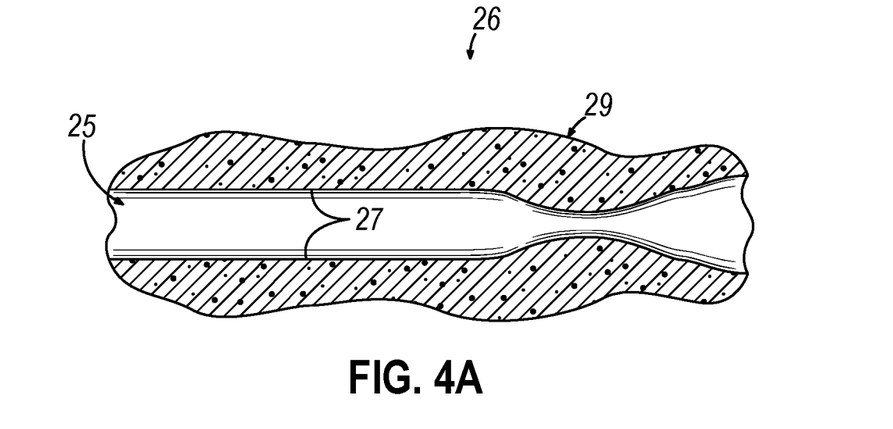
FIG. 4A depicts a cross-sectional view of a patulous Eustachian tube of a patient.
Figure 4B:
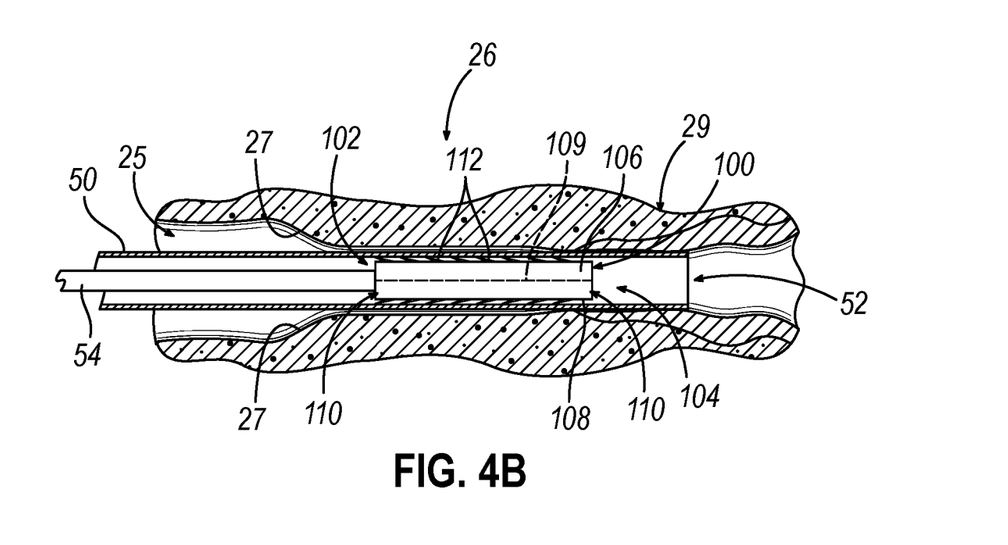
FIG. 4B depicts a cross-sectional view of the Eustachian tube of FIG. 4A, with a sheath slidably advanced therein, the sheath containing the implant of FIG. 2 therein, with the implant restricted to a contracted state by the sheath.

Barbs (112) are resiliently flexible to transition between a natural expanded state (see FIGS. 2-3 and 4C-4E) and a compressed state (see FIG. 4B). In particular, barbs (112) may be contained within a sheath (50) in the compressed state during deployment of implant (100), and then naturally return to the expanded state when barbs (112) are no longer contained within sheath (50). Barbs (112) may be configured to anchor implant (100) to ET (26) by penetrating portions of interior wall (27). Alternatively, barbs (112) may be configured anchor to ET (26) via any other suitable means as would be apparent to one skilled in the art in view of the teachings herein. For instance, barbs (112) may be configured to abut against interior wall (27) with sufficient frictional forces to anchor implant (100).

Conformable body (106) is a hollow cylindraceous body that extends along a longitudinal axis from a proximal portion (102) to a distal portion (104). Conformable body (106) includes exterior surface (108) and an interior surface (109). Exterior surface (108) is configured to contact interior wall (27) of ET (26) in order to impose a radially outward stress on a patulous ET (26) in a manner sufficient to maintain the position of conformable body (106) in the ET (26). Interior surface (109) extends from an open end at proximal portion (102) to an open end at distal portion (104). Interior surface (109) defines a collapsible vent pathway (110) that is configured to transition between an occluding, collapsed position (see FIG. 4D) and an expanded, ventilating state (see FIG. 4E) in order to relieve any pressure imbalance between the middle ear (14) and the pharyngeal ostium (28).

While the longitudinal profile of conformable body (106) is shown in a straight, linear arrangement in FIG. 2, conformable body (106) may flex to form other suitable longitudinal profiles, such as an S-shaped arrangement as shown in FIG. 3. Therefore, when implant (100) is suitably deployed within ET (26), conformable body (106) may contact interior wall (27) of ET (26) in such a manner that conformable body (106) defines a longitudinal profile similar to the longitudinal profile of ET (26). The flexible longitudinal profile may help reduce pain and or discomfort experienced by the patient during or after implant (100) has been deployed within ET (26).

Figure 4C:
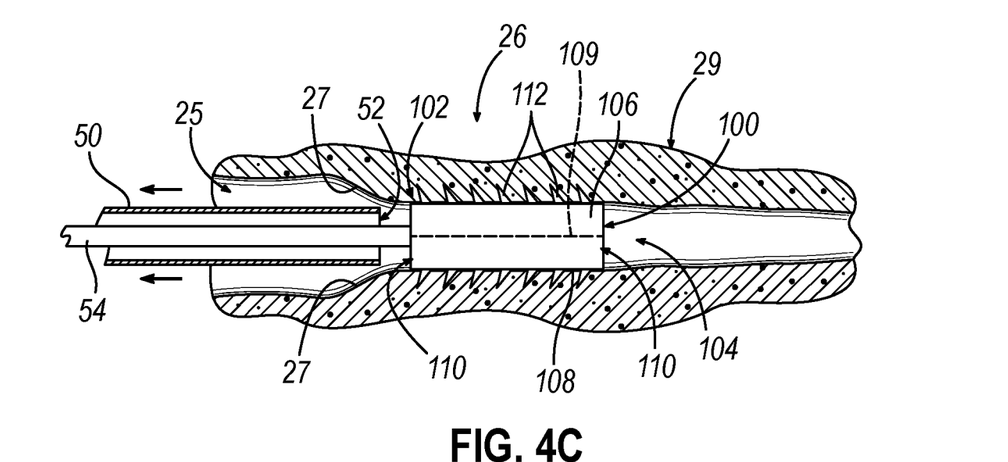
FIG. 4C depicts a cross-sectional view of the Eustachian tube of FIG. 4A, where the sheath of FIG. 4B is partially removed such that the implant of FIG. 2 inserted within the Eustachian tube is in an expanded state, thereby bearing against the side walls of the Eustachian tube.

Conformable body (106) is configured to be compressible. As seen in FIGS. 2-3 and 4E, exterior surface (108) of first body (106) is biased to naturally be in an expanded or enlarged state by default, while collapsible vent pathway (110) is configured to naturally be in the expanded, ventilating state. Conformable body (106) is formed of an elastomeric material that has elastic properties allowing conformable body (106) to be compressible between the expanded state (see FIG. 4C) and a compressed state (see FIG. 4B). In other words, conformable body (106) is configured to be radially compressed when compressed from the expanded state to the compressed state. For instance, conformable body (106) may be operable to radially compress and axially stretch to a smaller profile upon the application of a predetermined force onto exterior surface (108) of conformable body (106), thereby transitioning conformable body (106) from the expanded state into the compressed state. Some variations of conformable body (106) are non-compressible.

When implant (100) is suitably deployed, exterior surface (108) of conformable body (106) is dimensioned to abut against an interior wall (27) of ET (26) such that conformable body (106) bears against ET (26). In some scenarios, conformable body (106) slightly stretches or expands ET (26). Conformable body (106) may have any suitable dimension, while in the expanded state, as would be apparent to one skilled in the art in view of the teachings herein. For instance, conformable body (106) may have a diameter ranging between about 5 millimeters to about 9 millimeters. Additionally, conformable body (106) may have a varying radial dimension along the longitudinal profile of conformable body (106). The geometrical shape of conformable body (106) may have any suitably shape that would be apparent to one skilled in the art in view of the teachings herein. Conformable body (106) may be in the compressed state while contained within a sheath (50) during deployment of implant (100). Conformable body (106) may then naturally return to the expanded state when no longer contained within sheath (50). As will be described in greater detail below, containing conformable body (106) within sheath (50) during deployment of implant (100) may allow conformable body (106) to be initially inserted within the desired location of ET (26) without causing unnecessary discomfort for the patient.

While conformable body (106) is sufficiently resilient to transition between the naturally expanded state and the compressed state, conformable body (106) may also be sufficiently resilient such that when deployed within ET (26), exterior surface (108) of conformable body (106) maintains sufficient contact with interior wall (27) to suitably bear outwardly against ET (26). In other words, conformable body (106) is sufficiently flexible to transition into the compressed state within the confines of sheath (50), but also sufficiently resilient to bear outwardly against interior walls (27) of ET (26) while in the expanded state.

It should be understood that when the patient is not swallowing, yawning, etc., and implant (100) is suitably deployed within ET (26) in accordance with the description herein, conformable body (106) may still be under at least some degree of compression due to contact between exterior surface (108) of conformable body (106) and interior wall (27) of ET (26). In other words, the outer diameter (or perimeter) of exterior surface (108) is dimensioned slightly larger than the inner diameter (or perimeter) of interior wall (27) while a patient is not swallowing, yawning, etc. It should also be understood that conformable body (106) may be under even less compression, or not compressed as all, when the patient swallows, yawns, or does something else that would result in a temporary opening of a normally functioning ET (26).

Interior surface (109) defining collapsible vent pathway (110) is configured to remain in an occluding, collapsed position (see FIG. 4D) while exterior surface (108) of conformable body (106) is under compression due to contact with interior wall (27) of ET (26) when the patient is not swallowing, yawning, etc. Contact between exterior surface (108) and interior wall (27) while the patient is not swallowing, yawning, etc., allows exterior surface (108) to suitably impose a radially outward stress on interior wall (27) of ET (26) in accordance with the description herein. While in the occluded, collapsed position, interior surface (109) is sufficiently occluded to suitably inhibit fluid communication between the middle ear (14) and the pharyngeal ostium (28). Although collapsible vent pathway (110) is configured to naturally be in the expanded, ventilating state, the compression of exterior surface (108) imparted by interior wall (27) of ET (26) while the patient is not swallowing, yawning, etc., forces collapsible vent pathway (110) into the occluding, collapsed position.

As mentioned above, interior surface (109) defining vent pathway (110) may transition from the occluding, collapsed state (see FIG. 4D) into the expanded, ventilating state (see FIG. 4E) to relieve any pressure imbalance between the middle ear (14) and the pharyngeal ostium (28). As also mentioned above, in instances where the patient sneezes, coughs, yawns, etc., conformable body (106) may be under less compression, or not compressed at all. When a sufficient pressure imbalance is presented between the middle ear (14) and the pharyngeal ostium (28), or in instances where conformable body (106) is under less compression form interior wall (27) of ET (26), such as when the patient sneezes, coughs, yawns, etc., interior surface (109) defining vent pathway (110) is configured to transition from the collapsed, occluded state (see FIG. 4D) into an expanded, ventilated state (see FIG. 4E).

While in the expanded, ventilated state, vent pathway (110) defined by interior surface (109) may provide sufficient fluid communication between the middle ear (14) and the pharyngeal ostium (28) to relieve any undesirable pressure imbalance. In other words, implant (100) is configured to assist a patulous ET (26) in normally functioning as a pressure equalizing valve.

In some instances, implant (100) may be formed from a bioabsorbable material, such that implant (100) configured to completely absorb after any suitable period of time from initial deployment as would be apparent to one skilled in the art in view of the teachings herein. As one example, conformable body (106) may be formed from a material configured to completely absorb after about nine to twelve months. In other instances, implant (100) or selected portions of implant (100) may be formed from a non-bioabsorbable material. In such instances, implant (100) may be configured to be permanently attached, or implant (100) may be configured to be removed from the patient at a later time. Different portions of implant (100) may be formed from different materials. For example, conformable body (106) may be formed from a first material, bioabsorbable or non-bioabsorbable, and barbs (112) may be formed from a second material, bioabsorbable or non-bioabsorbable.

The entirety of implant (100), or selected portions of implant (100), may be coated or otherwise implemented with any suitable drug or therapeutic agent as would be apparent to one skilled in the art in view of the teachings herein. For example, conformable body (106) may be coated with a therapeutic agent. As another mere example, barbs (112) may be coated with a therapeutic agent. In versions incorporating a therapeutic agent, the therapeutic agent may be configured for immediate release. Alternatively, the therapeutic agent may be configured for delayed release. Alternatively, the therapeutic agent may be configured for sustained delivery over a certain period of time. Some versions may include more than one therapeutic agent, with the different therapeutic agents having different release times or release rates.

FIGS. 4A-4F show an exemplary deployment and use of implant (100) with a patulous ET (26). FIG. 4A shows ET (26) in a patulous state. First, as shown in FIG. 4B, an operator may advance a deployment mechanism containing implant (100) transnasally or transorally into ET (26) via the pharyngeal ostium (28). In the present example, deployment mechanism includes a sliding sheath (50) comprising an open distal end (52), and a push rod (54) located within the confines of sliding sheath (50). Implant (100) is constrained within sliding sheath (50). Sliding sheath (50) is advanced within channel (25) of ET (26) until implant (100) is suitably adjacent to interior walls (27) as shown in FIG. 4B. Any suitable deployment mechanism may be used as would be apparent to one skilled in the art in view of the teachings herein.

Implant (100) is housed within sliding sheath (50) such that distal portion (104) located proximal to open distal end (52) of sliding sheath (50), and such that barbs (112) are in the compressed state within sliding sheath (50). In some other variations, the inner diameter of sheath (50) is sized such that barbs (112) are not compressed within sliding sheath (50), even though barbs (112) are fully contained within sliding sheath (50). Conformable body (106) is confined in the compressed state within sliding sheath (50). A distal end of push rod (54) may be adjacent to the proximal end of conformable body (106) when sliding sheath (50) is advanced into ET (26). When implant (100) is positioned within ET (26) at the desired location, the operator may utilize deployment mechanism to suitably deploy implant (100) within ET (26). In the current example, and shown between FIGS. 4B-4D, the operator may slide sheath (50) proximally while push rod (54) remains stationary in contact with the proximal end of conformable body (106). Push rod (54) therefore keeps implant (100) longitudinally stationary within ET (26) while sheath (50) is retracted proximally relative to ET (26). Alternatively, the operator may actuate push rod (54) distally while keeping sheath (50) stationary, thereby distally advancing implant (100) out of open distal end (52) of sheath (50).

Figure 4D:
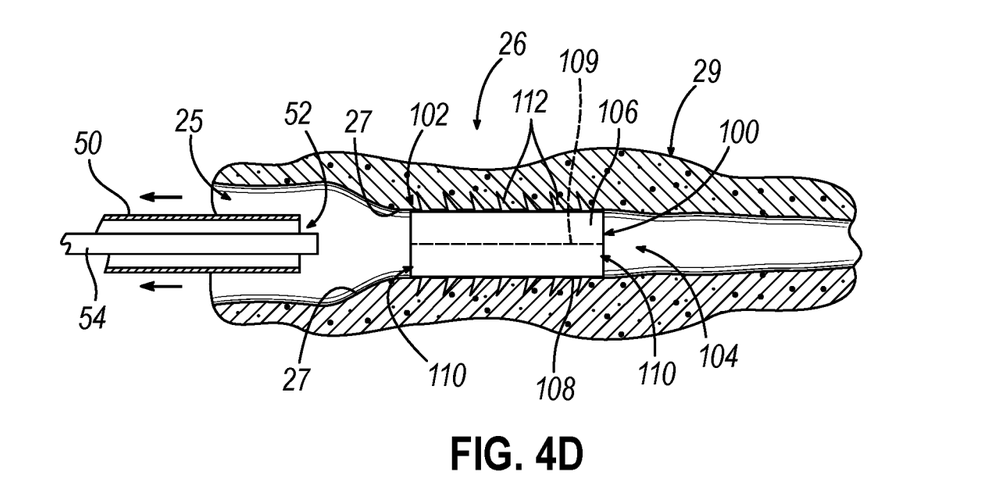
FIG. 4D depicts a cross-sectional view of the Eustachian tube of FIG. 4A, where the sheath of FIG. 4B is removed, and the implant of FIG. 2 is inserted within the Eustachian tube in the expanded state, thereby bearing against the side walls of the Eustachian tube, where the implant is in a collapsed position such that a vent pathway is occluded.
Figure 4E:
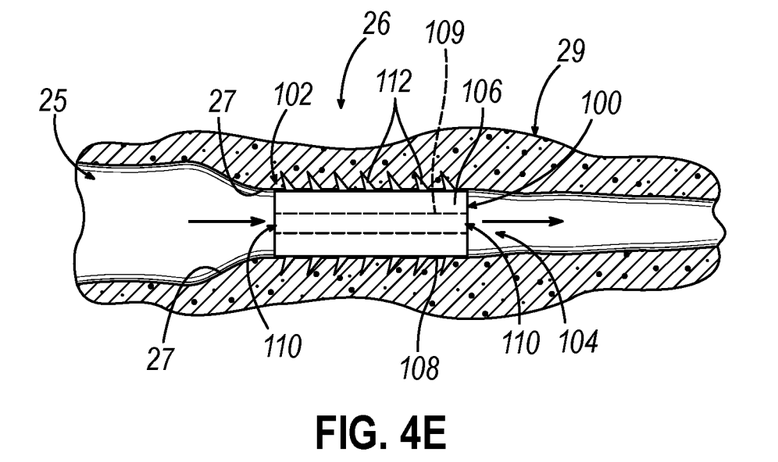
FIG. 4E depicts a cross-sectional view of the Eustachian tube of FIG. 4A, where the sheath of FIG. 4B is removed, and the implant of FIG. 2 is inserted within the Eustachian tube in the expanded state, thereby bearing against the side walls of the Eustachian tube, where the implant is in an expanded position such that the vent pathway of FIG. 4D is opened.
Figure 4F:
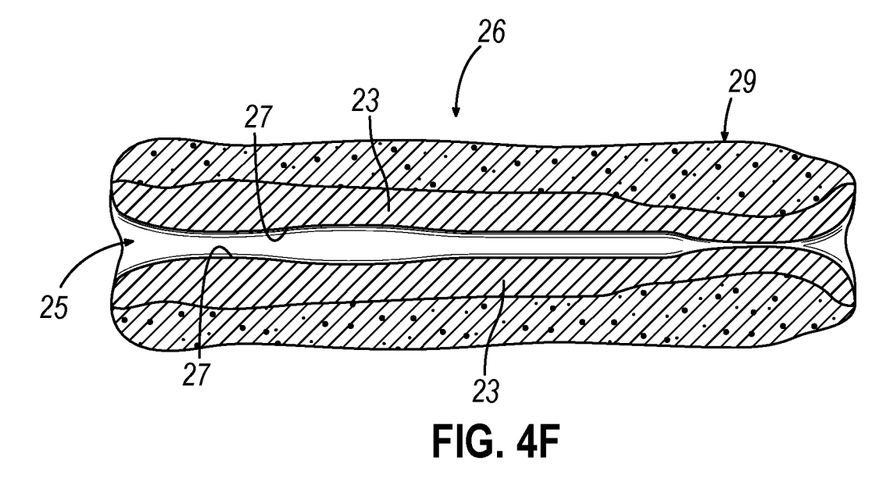
FIG. 4F depicts a cross-sectional view of the Eustachian tube of FIG. 4A, with the Eustachian tube in a normally functioning state after the implant of FIG. 2 has been bio-absorbed, where the Eustachian tube has regenerated cell growth.

Either way, when implant (100) is deployed, as shown in FIG. 4D, barbs (112) and conformable body (106) are no longer constrained in the compressed position such that barbs (112) and conformable body (106) resiliently return to the natural expanded position. In the current example, with barbs (112) in the natural expanded position, barbs (112) penetrate interior wall (27) to help initially anchor implant (100) within ET (26). As mentioned above, conformable body (106) bears outwardly against interior wall (27) of ET (26) while conformable body (106) is in the natural expanded position. In some cases, conformable body (106) increases the inner diameter defined by interior wall (27) by stretching or compressing the tissue of interior wall (27). The radial stress imposed by conformable body (106) on interior wall (27) may cause the generation of additional tissue (23) (e.g., scar tissue) in the ET (26).

As also mentioned above, interior surface (109) defining collapsible vent pathway (110) is configured to remain in an occluded, collapsed position (see FIG. 4D) while exterior surface (108) imposes a radially outward stress on interior wall (27) of ET (26). Once a sufficient pressure imbalance is presented between the middle ear (14) and the pharyngeal ostium (28), or in instances where conformable body (106)

is under less compression from interior wall (27) of ET (26), such as when the patent sneezes, yawns, coughs, etc., interior surface (109) defining vent pathway (110) transitions into an expanded, ventilated state (see FIG. 4E) to provide sufficient fluid communication between middle ear (14) and pharyngeal ostium (28). Once the pressure imbalance is relieved, or when interior wall (27) of ET (26) transitions back to a position associated with the patient not swallowing, yawning, etc., interior surface (109) may transition back into the occluded, collapsed position (see FIG. 4D).

After a suitable period of time, as shown in FIG. 4E, implant (100) may be bio-absorbed into adjacent anatomy. The additional tissue (23) may regenerate in response to stress imposed by conformable body (106) on ET (26), thereby providing ET (26) in a non-patulous state. In other words, the additional tissue (23) generated in response to stress imposed by conformable body (106) results in ET (26) transitioning from a patulous state to a normal functioning state.

It should be understood that, while implant (100) is bio-absorbed into adjacent anatomy, and additional tissue (23) is regenerated such the ET (26) transitions form a patulous state to a non-patulous state in the current example, this is merely optional. In some instances, implant (100) may provide permanent implantation such that implant (100) is never removed from (ET) or is never bio-absorbed into adjacent anatomy. In further instances, implant (100) may be removed or bio-absorbed, but the presence of implant (100) may not necessarily result in grown of additional tissue (23) or may not necessarily result in ET (26) reaching the state shown in FIG. 4E.

While implant (100) is described above as being formed of a bioabsorbable material, some other variations, may be formed of a non-bioabsorbable material. Thus, implant (100) need not necessarily be formed of bioabsorbable material in all cases. Regardless of whether implant (100) is bioabsorbable or non-bioabsorbable, implant (100) may include various kinds of expandable structures including but not limited to mesh, barbs (112), flanges, porous materials, compressible materials, or various other structures as will be apparent to those skilled in the art in view of the teachings herein.

B. Exemplary Implants with Alternative Ventilation Features

In some instances, it may be desirable for implant (100) to provide sufficient ventilation between middle ear (14) and pharyngeal ostium (28) without transitioning between an occluded and non-occluded state. In other words, it may sometimes be desirable for implant (100) to provide a constant ventilation between middle ear (14) and pharyngeal ostium (28), without necessarily providing the ET (26) in an undesirably persistently patulous state.

Figure 5:
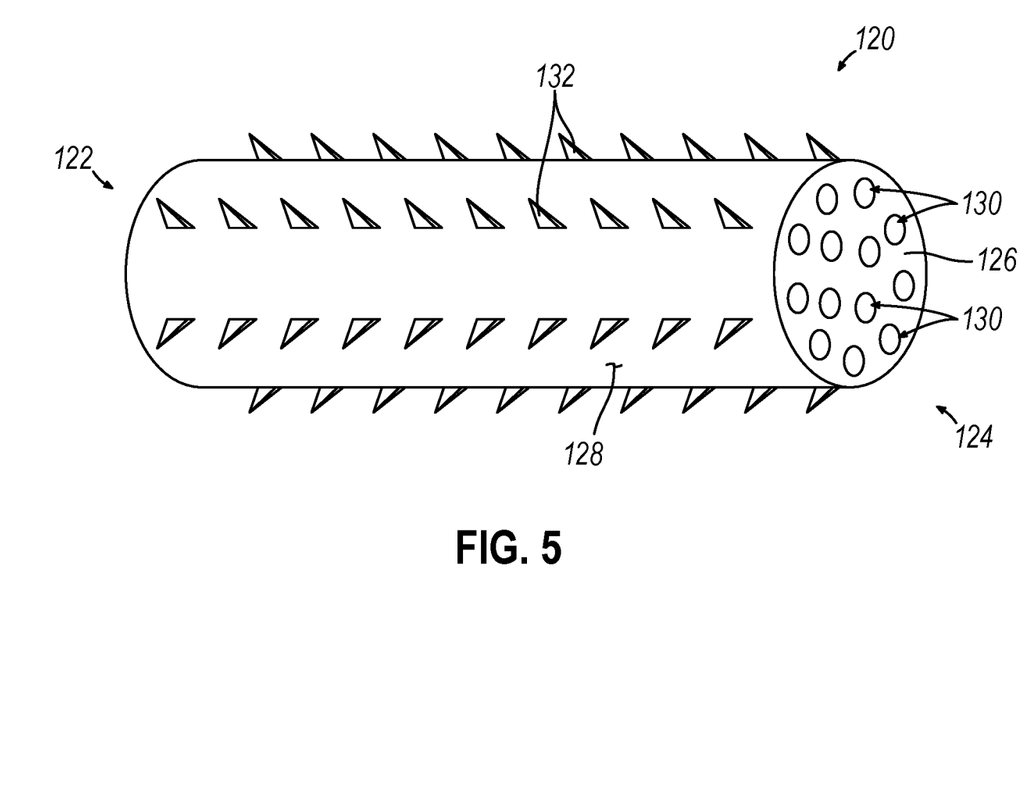
FIG. 5 depicts a perspective view of an alternative implant that may be used in replacement of the implant of FIG. 2.

FIG. 5 shows another implant (120) that may be implanted into ET (26) of a patient. Implant (120) may be substantially similar to implant (100) described above, with differences elaborated below. In particular, implant (120) includes a plurality of ventilation pathways (130) configured to provide ventilation between middle ear (14) and pharyngeal ostium (28).

Implant (120) extends from a proximal portion (122) to a distal portion (124), and includes a conformable body (126) having an exterior surface (128), and a plurality of barbs (132), which are substantially similar to proximal portion (102), distal portion (104), conformable body (106), exterior surface (108), and plurality of barbs (112) described above, with differences elaborated below.

Barbs (132) are resiliently flexible to transition between a natural expanded state and a compressed state. In particular, barbs (132) may be contained within a sheath (50) in the compressed state during deployment of implant (120), and then naturally return to the expanded state when barbs (132) are no longer contained within sheath (50). Barbs (132) may be configured to anchor implant (120) to ET (26) by penetrating portions of interior wall (27) in the expanded state.

Additionally, conformable body (126) is sufficiently resilient to transition between the naturally expanded state and the compressed state. Conformable body (126) may also be sufficiently resilient such that when deployed within ET (26), exterior surface (128) of conformable body (126) maintains sufficient contact with interior wall (27) to suitably bear outwardly against ET (26).

However, instead of conformable body (126) having an interior surface defining a collapsible vent, conformable body (126) defines a plurality of ventilation pathways (130) that provide ventilation when implant (120) is suitably deployed within ET (26). Ventilation pathways (130) extend between open ends at both proximal portion (122) and distal portion (124). Therefore, when implant (120) is deployed within ET (26), ventilation pathways (130) provide suitable ventilation and pressure balance between middle ear (14) and pharyngeal ostium (28) in substantially similar manner to implant (100) described above. Ventilation pathways (130) may have any suitable dimension as would be apparent. In some instances, ventilation pathways (130) are microporous vents that remain open to serve as a pressure balancing feature between middle ear (14) and pharyngeal ostium (28).

Figure 6:
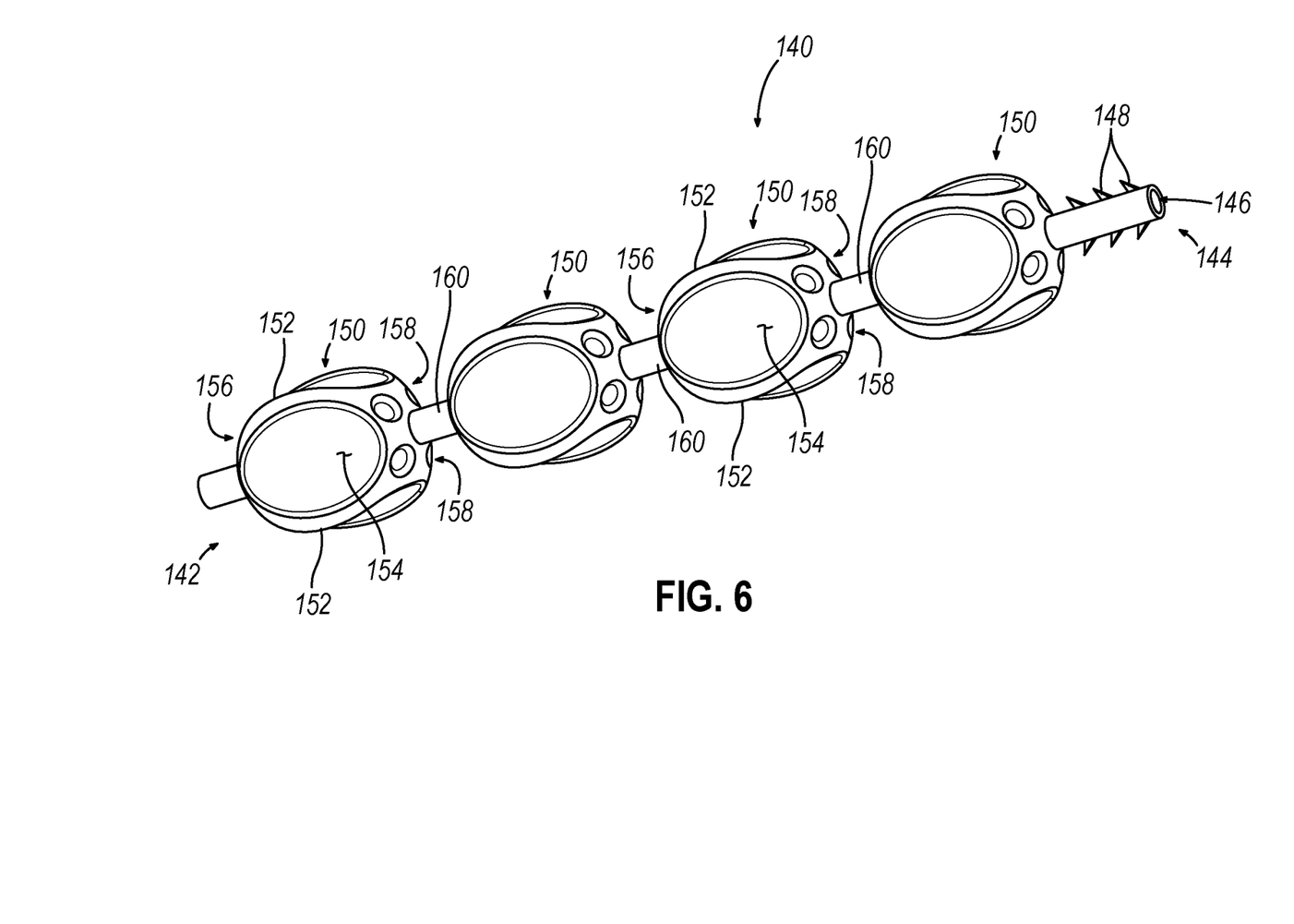
FIG. 6 depicts a perspective view of another alternative implant that may be used in replacement to the implant of FIG. 2.

FIG. 6 shows another exemplary implant (140) that may be implanted into ET (26) of a patient. As will be described in greater detail below, implant (140) includes various features that are configured to provide ventilation between middle ear (14) and pharyngeal ostium (28) when implant (140) is deployed within ET (26). As will be described in greater detail below, in some instance, ventilation features may be configured to provide constant ventilation between middle ear (14) and pharyngeal ostium (28); while in other instances, ventilation features may be configured to be temporarily opened when ET (26) momentarily enlarges due to the patient swallowing, yawning, etc.

Implant (140) extends along a longitudinal dimension from a proximal portion (142) to a distal portion (144). As will be described in greater detail below, proximal portion (142) is dimensioned to bear against ET (26) of the patient between middle ear (14) and pharyngeal ostium (28), and in some cases slightly expand or stretch ET (26) of the patient when suitably deployed; while distal portion (144) is dimensioned to be inserted within isthmus (29) and is configured to attach to isthmus (29) of the patient to help promote stability of a deployed implant (140) within ET (26). As will be described in greater detail below, bodies (150) of implant (140) define an exterior ventilation pathway (156) and an interior ventilation pathway (158) when suitably deployed within ET (26) such that ventilation pathways (156, 158) provide ventilation between middle ear (14) and pharyngeal ostium (28) in order to allow pressure balance and ventilation.

Proximal portion (142) includes an array of bodies (150) connected to each other in a linear array via connecting links (160). Each body (150) includes a plurality of convex engagement surfaces (152) and at least one concave surface (154). When implant (140) is deployed within ET (26), convex engagement surfaces (152) abut against interior surface (27) of ET (26) such that convex engagement surfaces (152) of bodies (150) bear radially outwardly against ET (26). Additionally, concave surfaces (154) extend away from interior surface (27) of ET (26) in order to define exterior ventilation pathway (156). Exterior ventilation pathway (156) extends between proximal and distal ends of each respective body (150).

Additionally, each body (150) also defines a plurality of interior ventilation pathways (158) that extends between proximal and distal ends of each respective body (150). When implant (140) is suitably deployed, ventilation pathways (156, 158) provide ventilation between middle ear (14) and pharyngeal ostium (28) in order to allow pressure balance and ventilation.

In some instances, exterior ventilation pathway (156) is dimensioned such that tissue forming interior wall (27) of ET (26) may deform against concave surfaces (154), thereby effectively occluding ventilation pathway (156) or otherwise preventing fluid communication through ventilation pathway (156). In other instances, implant (140) may be dimensioned such that tissue forming interior wall (27) of ET (26) may deform into gaps between adjacent bodies (150) of implant (140) in order to effectively occlude ventilation pathways (156). In either case, once the patient swallows, yawns, etc., and ET (26) effectively enlarges momentarily, those ventilation pathways (156, 158) could be temporarily opened to allow fluid communication between middle ear (14) and pharyngeal ostium (28).

In other instances, exterior ventilation pathway (156) is configured to define a "constant" ventilation. When exterior ventilation pathway (165) is a "constant" ventilation pathway, exterior ventilation pathway (156) maybe large enough to permit pressure equalization, but small enough to avoid problems associated with a patulous ET (26).

Bodies (150) may have any suitable shape or structure as would be apparent to one skilled in the art in view of the teachings herein. For instance, bodies (150) may be semispherical, semi-cylindrical, etc. Bodies (150) may have any suitable dimension as would be apparent to one skilled in the art in view of the teachings herein. For instance, bodies (150) may have a diameter ranging from approximately 1 millimeters and approximately 5 millimeters. Additionally, one body (150) may have different dimensions compared to other bodies (150) of the same implant (140). For instance, bodies (150) may have outer diameters that progressively reduce or increase along the length of implant (140), thereby providing implant (140) with a generally tapered longitudinal profile. Bodies (150) may be resiliently flexible such that bodies (150) may transition between a naturally expanded state (as shown in FIGS. 2 and 4C) and a compressed state (as shown in FIG. 4B). Bodies (150) may be radially compressed and axially lengthened when in the compressed state as compared to the naturally expanded state.

In the present example, bodies (150) may be in the compressed state while contained within a sheath (50) during deployment of implant (140). Bodies (150) may then naturally return to the expanded state when no longer contained within sheath (50). As will be described in greater detail below, containing bodies (150) within sheath (50) during deployment of implant (140) may allow bodies (150) to be initially inserted within the desired location of ET (26) without causing unnecessary discomfort for the patient. While bodies (150) are sufficiently resilient to transition between the naturally expanded state and the compressed state, bodies (150) may also be sufficiently resilient such that when deployed within ET (26), convex engagement surfaces (152) maintain sufficient contact with interior wall (27) to suitably bear radially outwardly against ET (26). In other words, convex engagement surfaces (152) of bodies (150) are sufficiently flexible to transition into the compressed state within the confines of sheath (50), but also sufficiently resilient to bear radially outwardly against interior wall (27) of ET (26) while in the expanded state.

Bodies (150) may have any suitable geometric configuration as would be apparent to one skilled in the art in view of the teachings herein. For example, bodies (150) may have a solid sphere-like shape, a hollow spherical shell shape, a cylindrical shape, an ellipsoidal shape, etc. In the current example, proximal portion (142) has four bodies (150). However, any suitable number of bodies (150) may be used as would be apparent to one skilled in the art in view of the teachings herein.

Connecting links (160) extends between bodies (150) such that bodies (150) are tethered to adjacent bodies (150). Additionally, connecting links (160) are suitably laterally bendable and or flexible to allow bodies (150) to easily move relative to each other, thereby changing the longitudinal profile of proximal portion (142) of implant (140). Connecting links (160) are also short enough such that the distance between adjacent bodies (150) is suitable for bodies (150) to provide the needed expansion of ET (26) when implant is suitably deployed. In the present example, connecting links (160) are non-extensible.

In some versions, connecting links (160) are separate, discrete pieces extending between adjacent pairs of bodies (150), such that each links (160) terminates in the adjacent bodies (150). In addition, or in the alternative, one, more than one, or all links (160) may extend along the full length of proximal portion (142), such that one, more than one, or all links (160) span through all bodies (150). In some such versions, bodies (150) may slide longitudinally along the one or more links (160) extending through bodies (150). Other suitable relationships between bodies (150) and links (160) will be apparent to those of ordinary skill in the art in view of the teachings herein.

While the longitudinal profile of proximal portion (142) is shown with bodies (150) in a linear arrangement, bodies (150) may move relative to each other to form other suitable longitudinal profiles, such as an S-shaped arrangement. Therefore, when implant (140) is suitably deployed with ET (26), bodies (150) may contact interior wall (27) of ET (26) in such a manner that bodies (150) conform to the longitudinal profile of ET (26). The flexible longitudinal profile may help reduce pain and or discomfort experienced by the patient during or after implant (140) has been deployed within ET (26). In the current example, one connecting link (160) extends between each pair of adjacent bodies (150). However, any other suitable number of connecting links (160) may be used as would be apparent to one skilled in the art in view of the teachings herein. Additionally, different connecting links (160) may have different levels of flexibility as would be apparent to one skilled in the art in view of the teachings herein.

Distal portion (144) includes a distal anchor (146) and a plurality of barbs (148), which may both be formed of any suitable bio-absorbable material as would be apparent to one skilled in the art in view of the teachings herein. Distal anchor (146) extends from the most distal body (150). Distal anchor (146) is dimensioned for insertion within isthmus (29) of the patient when implant (140) is deployed. Barbs (148) are connected to and extend away from distal anchor (146). In the present example, barbs (148) extend outwardly and proximally along respective axes that are oblique to the central longitudinal axis of implant (140). Barbs (148) are configured to anchor to isthmus (29) when deployed such that implant (140) is secured within ET (26).

Figure 7A:
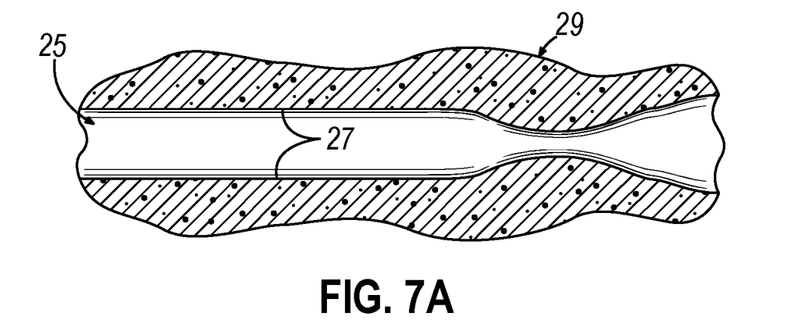
FIG. 7A depicts a cross-sectional view of a patulous Eustachian tube of a patient.
Figure 7B:
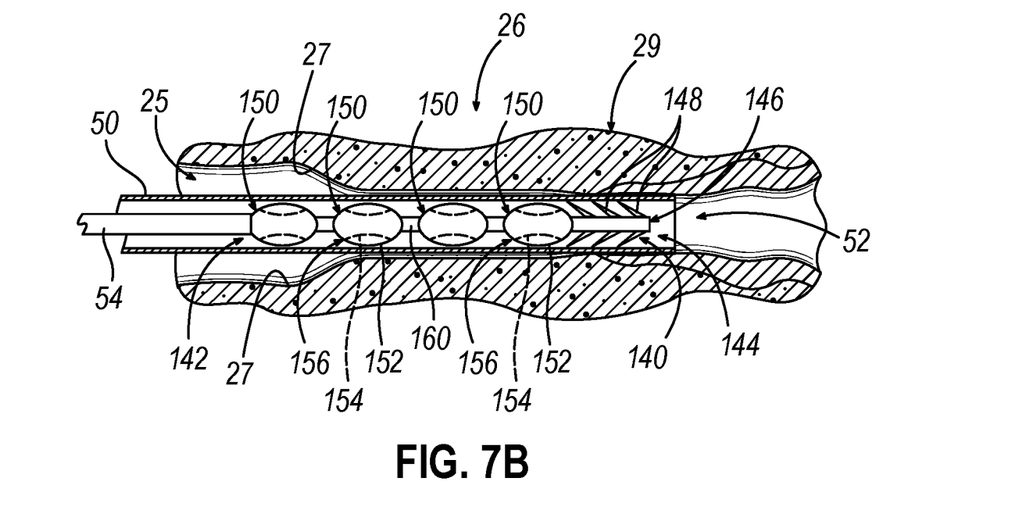
FIG. 7B depicts a cross-sectional view of the Eustachian tube of FIG. 7A, with a sheath slidably advanced therein, the sheath containing the implant of FIG. 6 therein, with the implant restricted to a contracted state by the sheath.
Figure 7C:
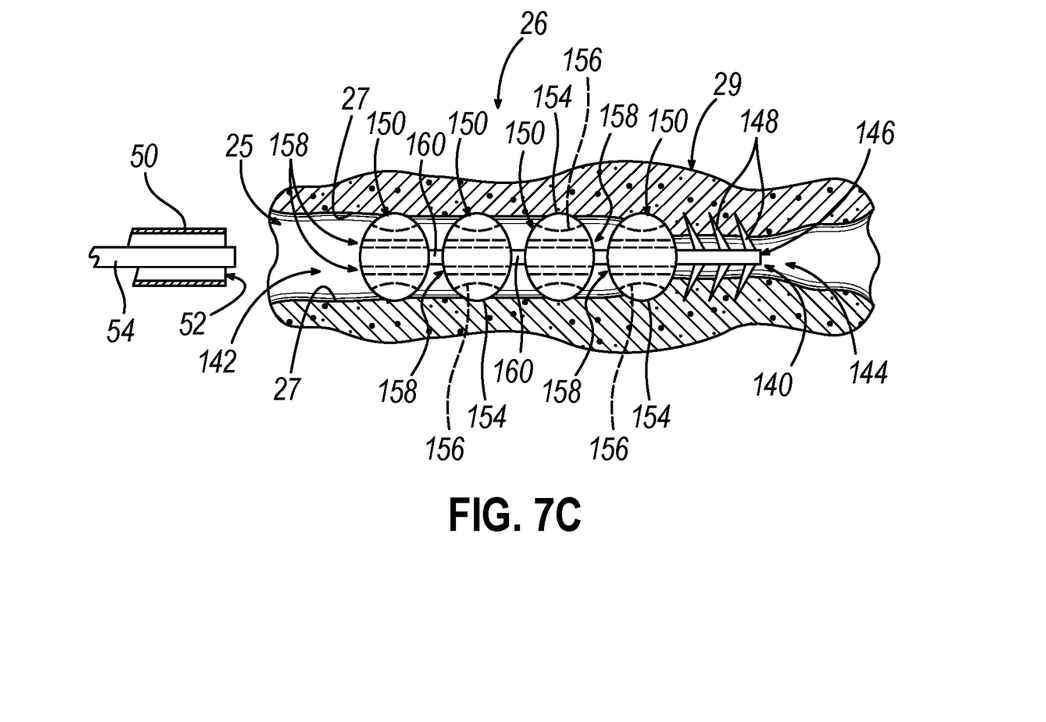
FIG. 7C depicts a cross-sectional view of the Eustachian tube of FIG. 7A, where the sheath of FIG. 7B is removed, and the implant of FIG. 6 is inserted within the Eustachian tube in the expanded state, thereby bearing against the side walls of the Eustachian tube.

Barbs (148) are resiliently flexible to transition between a natural expanded state (as shown in FIGS. 6 and 7C) and a compressed state (as shown in FIG. 7B). Barbs (148) may be contained within a sheath (50) in the compressed state during deployment of implant (140), and then naturally return to the expanded state when barbs (148) are no longer contained within sheath (50). In some other variations, barbs (148) are not compressed within sheath (50); and are merely contained within sheath (50) until deployment. Barbs (148) may be configured to anchor to isthmus (29) by penetrating portions of isthmus (29). Alternatively, barbs (148) may be configured anchor to isthmus (29) via any other suitably means as would be apparent to one skilled in the art in view of the teachings herein. For instance, barbs (148) may be configured to abut against interior wall of isthmus (29) with sufficient frictional forces to anchor implant (140). In some instances, bodies (150) may include barbs (148).

While in the current example, barbs (148) extend away from distal anchor (146) in a linear fashion, barbs (148) and distal anchor (146) may have any geometrical arrangement as would be apparent to one skilled in the art in view of the teachings herein. As one example, distal anchor (146) and barbs (148) may be replaced with a helical coil with spikes disposed about the coil such that the coil abuts against isthmus (29) while the spikes penetrate isthmus (29).

In some instances, implant (140) may be formed from a bioabsorbable material, such that implant (140) configured to completely absorb after any suitable period of time from initial deployment as would be apparent to one skilled in the art in view of the teachings herein. As one example, conformable body (146) may be formed from a material configured to completely absorb after about nine to twelve months. In other instances, implant (140) or selected portions of implant (140) may be formed from a non-bioabsorbable material. In such instances, implant (140) may be configured to be permanently attached, or implant (140) may be configured to be removed from the patient at a later time. Different portions of implant (140) may be formed from different materials. For example, bodies (150) may be formed from a first material, bioabsorbable or non-bioabsorbable, and barbs (148) may be formed from a second material, bioabsorbable or non-bioabsorbable.

The entirety of implant (140) or selected portions of implant (140) may be coated or otherwise implemented with any suitable drug or therapeutic agent as would be apparent to one skilled in the art in view of the teachings herein. For example, bodies (150) may be coated with a therapeutic agent. As another mere example, barbs (148) may be coated with a therapeutic agent.

FIGS. 7A-7D show an exemplary deployment and use of implant (140) with a patulous ET (26). FIG. 7A shows ET (26) in a patulous state. First, as shown in FIG. 7B, an operator may advance a deployment mechanism containing implant (140) transnasally or transorally into ET (26) via the pharyngeal ostium (28). In the present example, the deployment mechanism includes a sliding sheath (50) comprising an open distal end (52), and a push rod (54) located within the confines of sliding sheath (50). Sliding sheath (50) is advanced within channel (25) of ET (26) until distal anchor (146) is located directly adjacent to isthmus (29) as shown in FIG. 47. Any suitable deployment mechanism may be used as would be apparent to one skilled in the art in view of the teachings herein.

Implant (140) is located within sliding sheath (50) such that distal anchor (146) is located proximal to open distal end (52) of sliding sheath (50) such that barbs (148) are in the compressed state (or are otherwise contained) within sliding sheath (50). Similarly, bodies (150) are confined in the compressed state within sliding sheath (50). A distal end of push rod (54) may be adjacent to the most proximal body (150) when sliding sheath (50) is advanced into ET (26). When implant (140) is positioned within ET (26) at the desired location, the operator may utilize a deployment mechanism to suitably deploy implant (140) within ET (26). In the current example, the operator may slide sheath (50) proximally while push rod (54) remains stationary in contact with the proximal most body (150). Push rod (54) therefore keeps implant (140) longitudinally stationary within ET (26) while sheath (50) is retracted proximally relative to ET (26). Alternatively, the operator may actuate push rod (54) distally while keeping sheath (50) stationary, thereby distally advancing implant (140) out of open distal end (52) of sheath (50).

Either way, when implant (140) is deployed, as shown in FIG. 7C, distal barbs (148) and bodies (150) are no longer constrained in the compressed position such that barbs (148) and bodies (150) resiliently return toward the natural expanded position. In the current example, with barbs (148) in the natural expanded position, barbs (148) penetrate isthmus (29) to help initially anchor implant (140) within ET (26). As mentioned above, convex engagement surfaces (152) of bodies (150) bear radially outwardly against interior wall (27) of ET (26) in the natural expanded position, while connecting links (160) allow body (150) to move relative to each other such that bodies (150) conform to a longitudinal profile similar to that of ET (26). Additionally, concave surfaces (154) extend away from interior surface (27) of ET (26) in order to define exterior ventilation pathway (156), while bodies (150) also define interior ventilation pathways (158). ventilation pathways (156, 158) provide ventilation between middle ear (14) and pharyngeal ostium (28) in order to allow pressure balance and ventilation.

Figure 7D:
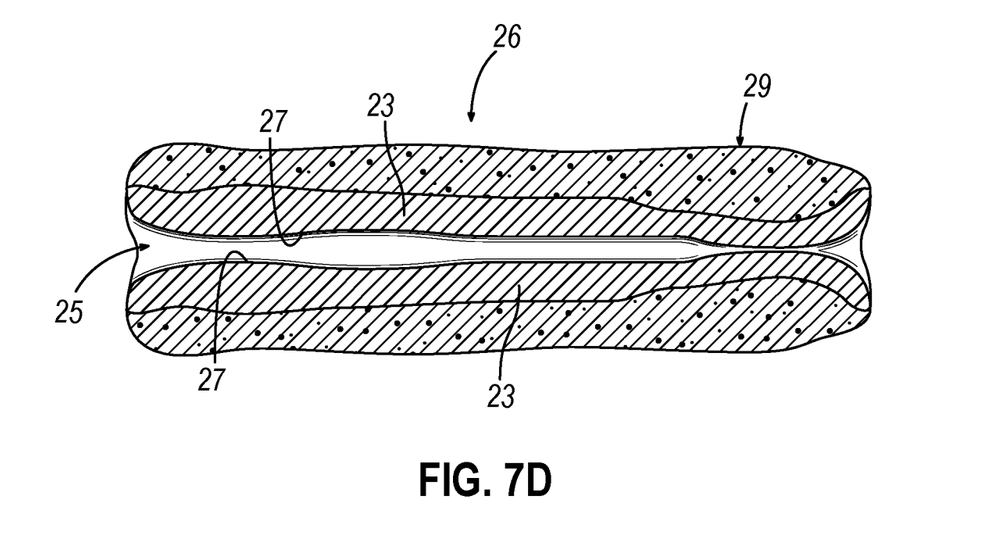
FIG. 7D depicts a cross-sectional view of the Eustachian tube of FIG. 7A, with the Eustachian tube in a normally functioning state after the implant of FIG. 6 has been bio-absorbed, where the Eustachian tube has regenerated cell growth.

After a suitable period of time, as shown in FIG. 7D, implant (140) may be bio-absorbed into adjacent anatomy. The additional tissue (23) may regenerate in response to stress imposed by on ET (26), thereby providing ET (26) in a non-patulous state. In other words, the additional tissue (23) generated in response to stress imposed by convex engagement surfaces (152) of bodies (150) results in ET (26) transitioning into a normal functioning state.

It should be understood that in the current example, implant (140) is bio-absorbed into adjacent anatomy, and additional tissue (23) is regenerated such the ET (26) transitions form a patulous state to a non-patulous state, this is merely optional. In some instances, implant (140) may provide permanent implantation such that implant (140) is never removed from (ET) or is never bio-absorbed into adjacent anatomy. In further instances, implant (140) may be removed or bio-absorbed, but the presence of implant (140) may not necessarily result in grown of additional tissue (23) or may not necessarily result in ET (26) reaching the state shown in FIG. 7D.

While implant (140) is described above as being formed of a bioabsorbable material, some other variations, may be formed of a non-bioabsorbable material. Thus, implant (140) need not necessarily be formed of bioabsorbable material in all cases. Regardless of whether implant (140) is bioabsorbable or non-bioabsorbable, implant (140) may include various kinds of expandable structures including but not limited to mesh, barbs (148), flanges, porous materials, compressible materials, or various other structures as will be apparent to those skilled in the art in view of the teachings herein.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An implant extending between proximal end and a distal end, wherein the implant is configured to maintain position within a Eustachian tube of a patient, the implant comprising: (a) an engagement body, wherein the engagement body comprises an exterior surface dimensioned bear radially outwardly against the Eustachian tube of the patient; (b) an anchoring assembly, wherein the anchoring assembly is configured to lock the implant in the Eustachian tube of the patient; and (c) a pressure balance assembly comprising a vented pathway configured to transition between an occluded state and a ventilated state, wherein the vented pathway is configured to provide fluid communication between the proximal end the distal end of the implant in the ventilated state, wherein the vented pathway is configured to inhibit fluid communication between the proximal end and the distal end of the implant in the occluded state.

Example 2

The implant of Example 1, wherein the pressure balance assembly comprises an interior surface of the engagement body, wherein the interior surface defines the vented pathway.

Example 3

The implant of Example 2, wherein the vented pathway is configured to transition between the occluded state and the ventilated state in response to a predetermined pressure differential between the proximal end and the distal end of the implant.

Example 4

The implant of any one or more of Examples 1 through 3, wherein the vented pathway is biased toward the ventilated state.

Example 5

The implant of any one or more of Examples 1 through 4, wherein the pressure balance assembly comprises an interior vent pathway extending between the proximal end and the distal end.

Example 6

The implant of Example 5, wherein the interior vent pathway comprises a microporous vent.

Example 7

The implant of any one or more of Examples 1 through 6, wherein the exterior surface of the engagement body defines a portion of the pressure balance assembly.

Example 8

The implant of any one or more of Examples 1 through 7, wherein the engagement body is coupled with a second engagement body via a connecting link.

Example 9

The implant of any one or more of Examples 1 through 8, wherein the engagement body comprises a compressible material configured to transition between a naturally expanded state and a constrained state.

Example 10

The implant of any one or more of Examples 1 through 9, wherein the implant is at least partially coated with a therapeutic agent.

Example 11

The implant of any one or more of Examples 1 through 10, wherein the anchoring assembly comprises a plurality of barbs extending from the second body.

Example 12

The implant of Example 11, wherein the plurality of barbs are resiliently coupled to the engagement body.

Example 13

The implant of any one or more of Examples 11 through 12, wherein the plurality of barbs further comprises an annular array of barbs.

Example 14

The implant of any one or more of Examples 11 through 13, wherein the plurality of barbs further comprises a linear array of barbs.

Example 15

The implant of any one or more of Examples 1 through 14, wherein the engagement body is configured to partially flex to change a longitudinal profile of the first body.

Example 16

The implant of any one or more of Examples 1 through 15, wherein the engagement is formed of a bioabsorbable material.

Example 17

The implant of any one or more of Examples 1 through 16, wherein implant is formed of a bioabsorbable material that is configured to bio-absorb after being deployed in the Eustachian tube for nine to twelve months.

Example 18

The implant of any one or more of Examples 1 through 17, further comprising a sheath configured to maintain the first body in a radially compressed state.

Example 19

An implant configured to bear radially outwardly against a Eustachian tube of a patient, the implant comprising: (a) a proximal end; (b) a distal end comprising a barbed anchor assembly; (c) a linear array of bodies arranged configured to transition between a compressed state and a naturally expanded state, wherein the linear array of bodies are dimensioned to bear radially outwardly against the Eustachian tube of the patient in the naturally expanded state; and (d) a pressure balance assembly, wherein at least a portion of the linear array of bodies defines the pressure balance assembly, wherein the pressure balance assembly is configured to provide fluid communication between a proximal end the distal end of the implant.

Example 20

An implant extending between proximal end and a distal end, wherein the implant is configured to maintain position within a Eustachian tube of a patient, the implant comprising: (a) an engagement body, wherein the engagement body comprises an exterior surface dimensioned bear radially outwardly against the Eustachian tube (b) a pressure balance assembly configured to transition between an occluded state and a ventilated state, wherein the pressure balance assembly is configured to provide fluid communication between the proximal end the distal end of the implant in the ventilated state, wherein the pressure balance assembly is configured to prevent fluid communication between the proximal end and the distal end of the implant in the occluded state.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implant extending between a proximal end and a distal end, wherein the implant is configured to maintain a position within an Eustachian tube of a patient, the implant comprising:
   (a) an engagement body, wherein the engagement body comprises an exterior surface dimensioned bear radially outwardly against the Eustachian tube of the patient;
   (b) an anchoring assembly, wherein the anchoring assembly is configured to lock the implant in the Eustachian tube of the patient; and
   (c) a pressure balance assembly comprising an interior surface of the engagement body which defines a vented pathway, wherein the vented pathway is configured to transition between an occluded state and a ventilated state in response to a predetermined pressure differential between the proximal end and the distal end of the implant, wherein the vented pathway is configured to provide fluid communication between the proximal end and the distal end of the implant in the ventilated state, wherein the vented pathway is configured to inhibit fluid communication between the proximal end and the distal end of the implant in the occluded state.

2. The implant of claim 1, wherein the vented pathway is biased toward the ventilated state.

3. The implant of claim 1, wherein the vented pathway comprises a microporous vent.

4. The implant of claim 1, wherein the exterior surface of the engagement body defines an exterior ventilation pathway.

5. The implant of claim 1, wherein the engagement body is coupled with a second engagement body via a connecting link.

6. The implant of claim 1, wherein the engagement body comprises a compressible material configured to transition between a naturally expanded state and a constrained state.

7. The implant of claim 1, wherein the implant is at least partially coated with a therapeutic agent.

8. The implant of claim 1, wherein the anchoring assembly comprises a plurality of barbs extending from the engagement body.

9. The implant of claim 8, wherein the plurality of barbs are resiliently coupled to the engagement body.

10. The implant of claim 8, wherein the plurality of barbs further comprises an annular array of barbs.

11. The implant of claim 8, wherein the plurality of barbs further comprises a linear array of barbs.

12. The implant of claim 1, wherein the engagement body is configured to partially flex to change a longitudinal profile of the engagement body.

13. The implant of claim 1, wherein the engagement body is formed of a bioabsorbable material.

14. The implant of claim 1, wherein implant is formed of a bioabsorbable material that is configured to bio-absorb after being deployed in the Eustachian tube for nine to twelve months.

15. The implant of claim 1, further comprising a sheath configured to maintain the engagement body in a radially compressed state.

16. An implant configured to bear radially outwardly against an Eustachian tube of a patient, the implant comprising:
(a) a proximal end;
(b) a distal end comprising a barbed anchor assembly;
(c) a linear array of bodies configured to transition between a compressed state and a naturally expanded state, wherein the linear array of bodies are dimensioned to bear radially outwardly against the Eustachian tube of the patient in the naturally expanded state; and
(d) a pressure balance assembly, wherein at least a portion of the linear array of bodies defines the pressure balance assembly, wherein the pressure balance assembly is configured to provide fluid communication between the proximal end and the distal end of the implant.

17. An implant extending between a proximal end and a distal end, wherein the implant is configured to maintain position within an Eustachian tube of a patient, the implant comprising:
(a) an engagement body, wherein the engagement body comprises an exterior surface dimensioned bear radially outwardly against the Eustachian tube;
(b) a pressure balance assembly comprising an interior surface of the engagement body which defines a vented pathway, wherein the vented pathway is configured to provide fluid communication between the proximal end and the distal end of the implant in a ventilated state, wherein the vented pathway is configured to prevent fluid communication between the proximal end and the distal end of the implant in an occluded state, wherein the vented pathway is configured to transition between the occluded state and the ventilated state in response to a determined pressure differential between the proximal end and the distal of the implant.

* * * * *